(12) United States Patent
Pines et al.

(10) Patent No.: US 6,211,188 B1
(45) Date of Patent: Apr. 3, 2001

(54) TREATMENT OF SKIN DISORDERS

(75) Inventors: Mark Pines, Rehovot; Arnon Nagler, Jerusalem, both of (IL)

(73) Assignee: Hadasit Medical Research Services and Development Company LTD, Jerusalem (IL)

(*) Notice: Subject to any disclaimer, the term of this patent is extended or adjusted under 35 U.S.C. 154(b) by 0 days.

(21) Appl. No.: 08/797,702

(22) Filed: Feb. 11, 1997

(51) Int. Cl.$^7$ .................................................. A61K 31/505
(52) U.S. Cl. .......................................... 514/259; 514/863
(58) Field of Search ..................................... 514/259, 863

(56) References Cited

U.S. PATENT DOCUMENTS 5,449,678 * 9/1995 Pines et al. ........................... 514/259

OTHER PUBLICATIONS

Knighton, et al, "Regulation of Cutaneous Wound Healing by Growth Factors and the Microenvironment", *Investigative Radiology*, vol. 26, No. 6,pp. 604–611 (1991).*

Haukipuro et al, "Synthesis of Typr I Collagen in Healing Wounds in Humans",*Ann of Surg.*, vol 213, No. 1 pp. 75–80, (1991).*

Granot et al, "Increased Skin Tearing in Broilers and Reduced Collagen Synthesis in Skin In Vivo and In Vitro In Response to the Coccidiostat Halofuginone", *Poultry Science*, 70:1559–1563 (1991).*

Ashcroft, The Effects of Ageing on Cutaneous Wound Healing in Mammals, *J. Anat.*, vol. 187, pp. 1–26, (1995).*

Choi et al, "Halofuginine, A Specific Collagen Type I Inhibitor, Reduces Anastomic Intimal Hyperplasia" *Arch. Surg.*, vol. 130, pp. 257–261, (1995).*

Freidman, et al "Regulation in Collagen Gene expression in Keloids and Hypertrophic Scars",*J. Surg. Res.*, 55:214–222 (1993).*

Rockwell, et al, "Keloids and Hypertrophic Scars: A Comprehensive Review", *Plastic and Recon. Surg.*, vol. 84, No. 5, pp. 827–836, (1989).*

Dauo–Brown, D.D., "Keloids: A Review of the Literature", *Brit. J. Plastic Surg.*, 43:70–77, (1990).*

Nagler, et al, "Inhibition of Collagen Synthesis, Smooth Muscle Cell Proliferation, and Injury–Induced Intimal Hyperplasia by Halofuginone", *Arter., Thromb. & Vasc. Biol.*, vol. 17, No. 1, pp. 1–9 (1997).*

Tulandi, T., "Prevention of Postoperative Intra–Abdominal Adhesions", *Curr. Opin. In Obst. & Gyn.*, 2:87–290,(1990).*

Menzies, D., "Postoperative Adhesions: Their Treatment and relevance in Clinical Practice", Ann. Roy. Col. Surg., vol. 75, 147–153, (1993).*

Drolette, et al, "Pathophysiology of Pelvic Adhesions", *J. Reprod. Med.*, vol. 37, No. 2, pp. 107–122 (1992).*

Monk et al, "Adhesions after Extensive Gyneclogic Surgery: Clinical Significance, Etiology and Prevention", *Am. J. Obstet.Gynecol*,vol. 170, No. 5, Part 1, pp. 1396–1403 (1994).*

Weinstein et al, "Cell Proliferation Kinetiks", no further information.*

Glinski et al, "Alteration of T–cell Extracellular Matrix Proteins interactions in Psiorasis",.*

Holz et al, "Inhibition of Peritoneal Adhesion Reformation After Lysis with Thirty–Two Percent Dextran 70", *Fertility and Sterility*, vol. 34, No. 4, pp. 394–395 (1980).*

Menzies et al, "Intral–Abdominal Adhesions and Thei Prevention by Topical Tissue Plasminogen Activator", *J. Roy. Soc. Med.*, vol. 82 pp. 534–535 (1989).*

Raftery, A.T., "Effect of Peritoneal Trauma on Peritoneal Fibrinolytic Activity and Intraperitoneal Adhesion Formation", *Eur. Surg. Res.*, 13:397–401 (1981).*

Rivkind et al, "Urokinase Does Not Prevent Abdominal Adhesion Formation in Rats", *Eur. Surg. Res.*, 17:254–258 (1985).*

Weibel et al, "Peritoneal Adhesions and their Relation to Abdominal Surgery",*Am. J. Of Surg.*, vol 126, pp 345–353 (1973.*

Gilmore et al "Prevention of Peritoneal Adhesions by a New Providone–Iodine/PVP Solution", J. Of Surg. Res., *J. Of Surg. Res.*, vol. 25, pp. 477–481 (1978).*

Rivkind et al, Cianidanol ([+]–Cianidanol–3) Prevents the Development of Abdominal Adhesions in Rats),*Arch. Surg.*, vol. 118, pp. 1431–1433 (1983).*

Menzies et al, "The Role Plasminogen Acrivator in Adhesion Prevention", *Surg. Gynecol. & Obstet.*, vol. 172, pp. 361–366 (1991).*

Brooks et al "Integrin $\alpha_v\beta_3$ Antagonists Promote Tumor Regression by Inducing Apoptosis of Angeogenic Blood Vessels", *Cell*, vol. 79, pp. 1157–1164 (1994).*

Folkman et al, "Angiogenesis", *J. Of Biological Che*, vol. 267 No. 16 pp. 109031–109109 (1992).*

Folkman et al, "Angiogenic Factors", *Science*, vol. 235, pp. 442–447 (1987).*

Folkman, J., "Toward an Understanding of Angiogenesis: Search & Discovery", *Persp. In Biol. & Med.*, pp. 11–37 (1985).*

Salo et al, "Effect of Phenytoin and Nifedipine on Collagen Gene expression in Human Gingival Fibroblasts",.*

(List continued on next page.)

Primary Examiner—Kevin E. Weddington
(74) Attorney, Agent, or Firm—Mark A. Friedman

(57) ABSTRACT

An effective treatment for skin disorders characterized by abnormal skin cell behavior, including a pharmaceutically effective amount of Halofuginone. Skin disorders which can be treated include keloids, hypertrophic scars, psoriasis, acne, seborrhea and alopecia. Halofuginone can reduce or eliminate clinical symptoms of these disorders, as well as substantially prevent the formation of keloids and hypertrophic scars.

6 Claims, 6 Drawing Sheets

OTHER PUBLICATIONS

Nickoloff et al, "Abberant Production of Interleukin–8 and Thrombospondin–1 by Psoriatic Keratinocytes Mediates Angiogenesis", *Am. J. Path.* vol. 144, No. 4, pp. 820–828 (1994).*

Mahadevan et al, "The Effects of Ovarian Adhesive Disease Upon Follicular Development in Cycles of Controlled Stimulation for In Vitro Fertilization", Fertility & Sterility, vol. 44, No. 4, pp. 489–492 (1985).*

Takahashi et al, "Cellular Markers That Distingui the Phases of Hemangioma during Infancy and Childhood", *J. Clin. Invest.,* vol. 93, pp. 2357–2364 (1994).*

Weidner et al, "Tumor Angiogenesis Correlates with Metastasis in Invasive Prostrate Carcinoma", *Am. J. Path.,* vol. 143, No. 2, pp. 401–409 (1993).*

Folkman, J., "What is the Evidence That Tumors are Angiogenesis dependent?", J. Nat'l. Cancer Inst., vol. 82, No. 1, pp. 4–6, (1989).*

Peacock et al, "Angiogenesis Inhibition Suppresses Collagen Arthritis", *J. Exp. Med.,* vol. 175, pp. 1135–1138 (1992).*

Miller et al, "Vascular Endothelial Growth factor/Vascular Permeability factor is tempoarilyand Spatially Correlated with Ocular Angiogenesis in a Primate Model",*Am. J. Path.,* vol. 145, No. 3, pp. 574–584 (1994).*

Folkman, J., "Angiogenesis in Cancer, Vascular, Rheumatoid and Other Disease", *Nature Medicine,* vol. 1, No. 1, pp. 27–31 (1995).*

Bischoff, J. "Approaches to Studying Cell Adhesion Molecules in Angiogenesis", *Trends in Cell Biol.,* vol. 5, pp. 69–74 (1995).*

Sawhney et al, "Optimization of Photopolymerized Bioerodable Hydrogel Properties for Adhesion Prevention", *J. Biomed. Mat. Res.,* vol. 28, pp. 831–838 (1994).*

Jackson et al, "Type I Collagen Fibrils Promote Rapid Vascular Tube Formation Upon Contact with the Apical Side of Cultured Endothelium", *Exp. Cell Res.,* 192:319–323 (1991).*

Iruela–Arispe et al, "Differential Expression of Extracellular Proteins is Correlated with Angiogenesis In Vitro", *Lab. Invest.,* vol. 64, No. 2, pp. 174–186 (1991).*

Ingber et al, "Synthetic Analogues of Fumagillin that Inhibit Angiogenesis and Suppress Tumor Growth", *Nature,* vol. 348, pp. 555–557 (1990).*

Castle et al, "Antisense–Mediated Reduction in Thrombospondin Reverses the Mlignant Phenotype of a Human Squamous Carcinoma", *J. Cli. Invest.,* vol. 87, pp. 1883–1888 (1991).*

Hill–West et al, "Efficacy of a Resorable Hydrogel Barrier, Oxidized Regenerated Cellulose, and Hyaluronic Acid in the Prevention of Ovarian Adhesions in a Rabbit Model", *Fertility & Sterility,* vol. 62, No. 3, pp. 630–634 (1994).*

Vick., "Statistics of Acute Intestinal Obstruction" *Brit. Med. J.,* pp. 546–548 (1932).*

* cited by examiner

Effect of halofuginone on ECM production by corneal endothelial cells
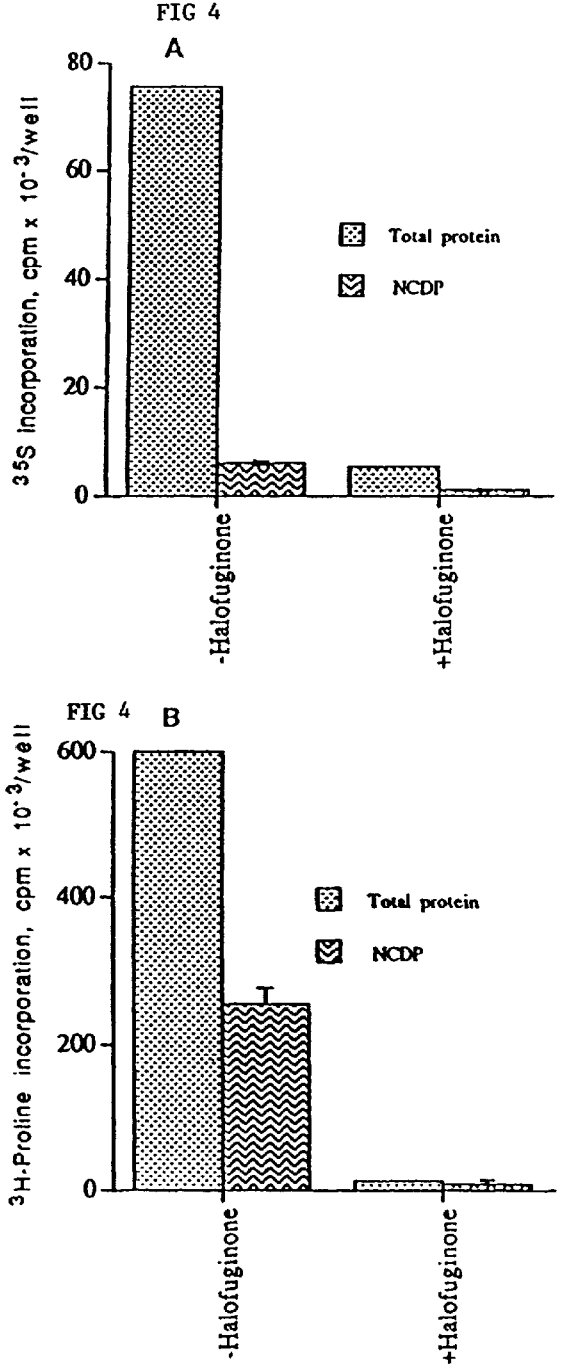
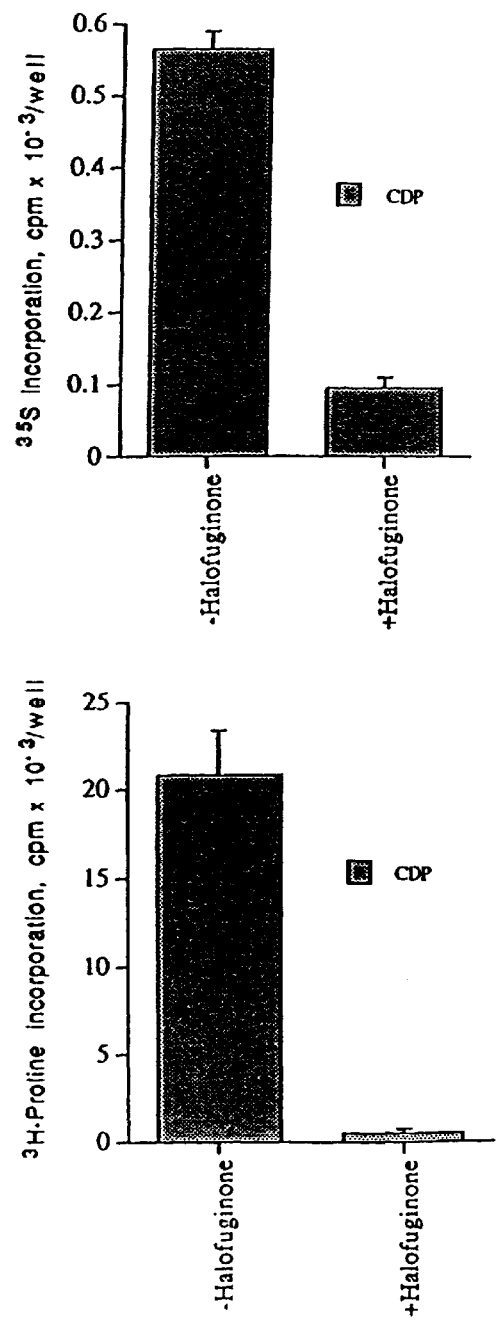
FIG 4 A
FIG 4 B Effect of halofuginone on ECM production by corneal endothelial cells

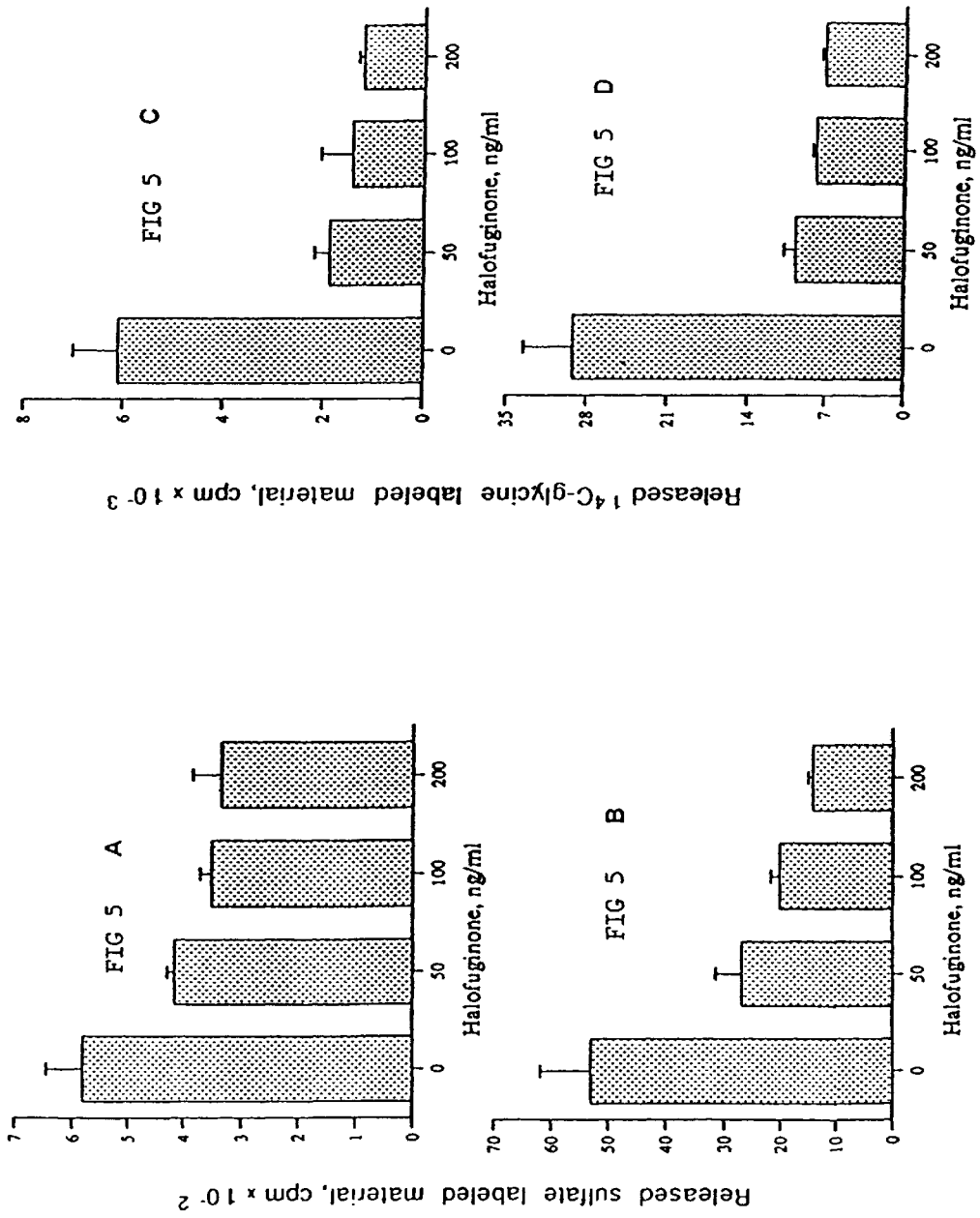

TREATMENT OF SKIN DISORDERS

FIELD AND BACKGROUND OF THE INVENTION

The present invention relates to a method and a composition for the treatment of skin disorders and, more particularly, to a method and a composition for the treatment and prevention of psoriasis, hypertrophic scars and keloids.

Keloids are benign fibrotic tumors which are believed to arise from the reticular dermis. They are characterized by increased tissue fibrosis and collagen deposition [Friedman, D. W. et al., J. Surg. Res., Vol. 55, p. 214–222, 1993]. Keloids usually first appear when a patient is between the ages of 10 and 30 years, and are often associated with trauma. They occur most commonly on the upper back, anterior chest, shoulders and ear lobes. Keloids are especially frequently seen in patients of African or Asian descent.

Hypertrophic scars are somewhat related to keloids, in that they are also characterized by increased tissue fibrosis and collagen deposition [Friedman, D. W. et al., J. Surg. Res., Vol. 55, p. 214–222, 1993]. Furthermore, hypertrophic scars are also most often seen in patients of African and Asian descent [Rockwell, W. B. et al., Plastic and Recon. Surg., Vol. 84, p 827–835, 1989]. Although there are certain differences between hypertrophic scars and keloids, such as a lower fibroblast density in keloids than in hypertrophic scars, a common mechanism is believed to underlie both conditions. Specifically, a genetically-determined aberration of the metabolism of melanocyte-stimulating hormone (MSH) is believed to be responsible for both hypertrophic scars and keloids [Rockwell, W. B. et al., Plastic and Recon. Surg., Vol. 84, p. 827–835, 1989]. Thus, both hypertrophic scars and keloids represent the effects of genetically abnormal behavior of skin cells.

Keloids and hypertrophic scars are characterized histologically by a rich vasculature, a high mesenchymal cell density, a thickened epidermis cell layer, and an abundance of collagen fibers. In hypertrophic scars, these fibers are loosely arrayed in a swirl-like pattern within bundles. In keloids, these fibers show even less organization, without any discrete bundles. By contrast, in normal skin these collagen fibers are arranged in distinct, clearly demarcated bundles.

The formation of both keloids and hypertrophic scars is marked by an initial infiltration of the traumatized tissue by fibroblasts, which is followed by the formation of a dense collagenous meshwork. Collagen production, as measured by prolyl hydroxylase activity, was found to be elevated in keloids, as compared to normal skin and normally healing wounds [Cohen, K. I. et al., Surg. Forum, Vol 22, p. 488, 1971]. Collagen synthesis was also found to be elevated in hypertrophic scars, but not to as great an extent [Rockwell, W. B. et al., Plastic and Recon. Surg., Vol. 84, p. 827–835, 1989]. The ratio of type I collagen to type III collagen was found to be significantly elevated in keloids but not hypertrophic scars, due to a specific increase in $\alpha 1(I)$ collagen gene expression, although type III collagen gene expression is also increased [Friedman, D. W. et al., J. Surg. Res., Vol. 55, p. 214–222, 1993; Rockwell, W. B. et al., Plastic and Recon. Surg., Vol. 84, p. 827–835, 1989]. Thus, clearly the deposition of collagen plays an important role in keloid and hypertrophic scar formation.

Similarly, psoriasis is also characterized by genetically-determined abnormal behavior of skin cells. Psoriasis is clinically marked by extensive scaling and a thickened epidermis [G. D. Weinstein and J. L. McCullough, Cell Proliferation Kinetics, p. 327–342]. These clinical manifestations are caused by hyperproliferation of epidermal cells. This hyperproliferation is also seen in non-psoriatic skin of psoriatic patients, indicating that the genetic defect is also present in apparently "normal" skin cells of psoriatic patients [G. D. Weinstein and J. L. McCullough, Cell Proliferation Kinetics, p. 327–342]. Although collagen also plays a role in the etiology of psoriasis, the abnormal hyperproliferation of epidermal cells is linked to the increased deposition of a number of extracellular matrix components, including collagen. Thus, clearly the inhibition of these extracellular matrix components could be an important factor in the inhibition of hyperproliferation by genetically abnormal psoriatic cells.

Keloids, hypertrophic scars and psoriasis thus have a number of characteristics in common. First, they represent a significant cosmetic problem, particularly on the face where they can be highly disfiguring and a source of considerable distress to the patient. Second, they can also be a source of discomfort through pruritus and even pain. Indeed, both keloids and hypertrophic scars can become so large that they are crippling [D. D. Datubo-Brown, Brit. J. Plas. Surg., Vol 43, p. 70–77, 1990]. Furthermore, although keloids on the cornea are rare, they can potentially result in blindness [D. D. Datubo-Brown, Brit. J. Plas. Surg., Vol 43, p. 70–77, 1990). Third, collagen plays a crucial, if varied, role in the development of all three conditions. Finally, all three conditions are caused by a genetic defect in skin cells, which causes these cells to show abnormal behaviors.

Unfortunately, currently available treatments to inhibit the formation and growth of keloids and hypertrophic scars, and to treat psoriasis, are not completely successful. For example, surgery can be used to reduce the size or extent of the lesion, while physical pressure can be used to reduce the size and extent of keloids and hypertrophic scars, as well as to prevent their initial formation [D. D. Datubo-Brown, Brit. J. Plas. Surg., Vol 43, p. 70–77, 1990). However, neither treatment can prevent the lesion from recurring, and surgery especially carries a risk of increased morbidity.

Other forms of treatment include the administration of corticosteroids. For example, triamcinolone appears to reduce the size of keloids and hypertrophic scars by increasing the rate of collagen degradation [Rockwell, W. B. et al., Plastic and Recon. Surg., Vol. 84, p. 827–835, 1989]. However, the side effects of such medications are potentially dangerous and are not universally successful. Other treatments, such as radiation, also showed variable effectiveness and are associated with other potential side effects [Rockwell, W. B. et al., Plastic and Recon. Surg., Vol. 84, p. 827–835, 1989]. Thus, clearly improved treatments for keloids and hypertrophic scars are required.

As noted above, collagen synthesis and deposition plays an important role in keloid and hypertrophic scar formation, as well as in the cell hyperproliferation associated with psoriasis. The synthesis of collagen is also involved in a number of other pathological conditions, particularly those associated with primary or secondary fibrosis. The crucial role of collagen in fibrosis has prompted attempts to develop drugs that inhibit its accumulation [K. I. Kivirikko, *Annals of Medicine*, Vol. 25, pp. 113–126 (1993)].

Such drugs can act by modulating the synthesis of the procollagen polypeptide chains, or by inhibiting specific post-translational events, which will lead either to reduced formation of extra-cellular collagen fibers or to an accumulation of fibers with altered properties. Unfortunately, only a few inhibitors of collagen synthesis are available, despite the importance of this protein in sustaining tissue integrity and its involvement in various disorders.

For example, cytotoxic drugs have been used in an attempt to slow the proliferation of collagen-producing fibroblasts (J. A. Casas, et al., *Ann. Rhem. Dis.,* Vol. 46, p. 763 (1987)], such as colchicine, which slows collagen secretion into the extracellular matrix [D. Kershenobich, et al., *N. Engl. J. Med.,* Vol. 318, p. 1709 (1988)], as well as inhibitors of key collagen metabolism enzymes [K. Karvonen, et al., *J. Biol Chem.,* Vol. 265, p. 8414 (1990); C. J. Cunliffe, et al., *J. Med. Chem.,* Vol. 35, p.2652 (1992)].

Unfortunately, none of these inhibitors are collagen-type specific. Also, there are serious concerns about the toxic consequences of interfering with biosynthesis of other vital collagenous molecules, such as Clq in the classical complement pathway, acetylcholine esterase of the neuro-muscular junction endplate, conglutinin and pulmonary surfactant apoprotein.

Other drugs which can inhibit collagen synthesis, such as nifedipine and phenytoin, inhibit synthesis of other proteins as well, thereby non-specifically blocking the collagen biosynthetic pathway [T. Salo, et al., *J. Oral Pathol. Med.,* Vol. 19, p. 404 (1990)].

Collagen cross-linking inhibitors, such as β-aminopropionitrile, are also non-specific, although they can serve as useful anti-fibrotic agents. Their prolonged use causes lathritic syndrome and interferes with elastogenesis, since elastin, another fibrous connective tissue protein, is also cross-linking. In addition, the collagen cross-linking inhibitory effect is secondary, and collagen overproduction has to precede its degradation by collagenase. Thus, a type-specific inhibitor of the synthesis of collagen itself is clearly required as an anti-fibrotic agent.

Such a type-specific collagen synthesis inhibitor is disclosed in U.S. Pat. No. 5,449,678 for the treatment of fibrotic conditions. This specific inhibitor is a composition with a pharmaceutically effective amount of a pharmaceutically active compound of a formula:

wherein:
  $R_1$ is a member of the group consisting of hydrogen, halogen, nitro, benzo, lower alkyl, phenyl and lower alkoxy;
  $R_2$ is a member of the group consisting of hydroxy, acetoxy and lower alkoxy, and
  $R_3$ is a member of the group consisting of hydrogen and lower alkenoxy-carbonyl.

Of this group of compounds, Halofuginone has been found to be particularly effective for such treatment.

U.S. Pat. No. 5,449,678 discloses that these compounds are effective in the treatment of fibrotic conditions such as scleroderma and Graft Versus Host Disease. WO Patent No. 96/06616 further discloses that these compounds are effective treatments for restenosis by preventing the proliferation of vascular smooth muscle cells. The two former conditions are associated with excessive collagen deposition, which can be inhibited by Halofuginone. Restenosis is characterized by smooth muscle cell proliferation and extracellular matrix accumulation within the lumen of affected blood vessels in response to a vascular injury [Choi et al., *Arch. Surg.,* Vol. 130, p. 257–261 (1995)]. One hallmark of such smooth muscle cell proliferation is a phenotypic alteration, from the normal contractile phenotype to a synthetic one. Type I collagen has been shown to support such a phenotypic alteration, which can be blocked by Halofuginone [Choi et al., *Arch. Surg.,* Vol. 130, p. 257–261 (1995), WO Patent No. 96/06616]. Thus, Halofuginone can prevent such redifferentiation of smooth muscle cells after vascular injury by blocking the synthesis of type I collagen.

There is thus a widely recognized unmet medical need for an inhibitor of keloid and hypertrophic scar formation, as well as for a treatment of already formed keloids and hypertrophic scars, which have specific inhibitory effects.

SUMMARY OF THE INVENTION

According to the present invention, there is provided a composition for treating a skin disorder characterized by substantially abnormal cell behavior, including a pharmaceutically effective amount of a compound in combination with a pharmaceutically acceptable carrier, the compound being a member of a group having a formula:

wherein:
  $R_1$ is a member of the group consisting of hydrogen, halogen, nitro, benzo, lower alkyl, phenyl, and lower alkoxy;
  $R_2$ is a member of the group consisting of hydroxy, acetoxy, and lower alkoxy, and
  $R_3$ is a member of the group consisting of hydrogen and lower alkenoxy.

According to another embodiment of the present invention, there is provided a composition for substantially preventing a skin disorder characterized by substantially abnormal cell behavior, including a pharmaceutically effective amount of a compound in combination with a pharmaceutically acceptable carrier, the compound being a member of a group having a formula:

wherein:
  $R_1$ is a member of the group consisting of hydrogen, halogen, nitro, benzo, lower alkyl, phenyl, and lower alkoxy;
  $R_2$ is a member of the group consisting of hydroxy, acetoxy, and lower alkoxy and
  $R_3$ is a member of the group consisting of hydrogen and lower alkenoxy.

According to yet another embodiment of the present invention, there is provided a method of manufacturing a medicament for treating a skin disorder characterized by substantially abnormal cell behavior, including the step of placing a pharmaceutically effective amount of a compound in a pharmaceutically acceptable carrier, the compound being a member of a group having a formula:

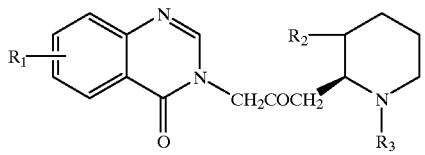

wherein:
- $R_1$ is a member of the group consisting of hydrogen, halogen, nitro, benzo, lower alkyl, phenyl, and lower alkoxy;
- $R_2$ is a member of the group consisting of hydroxy, acetoxy, and lower alkoxy, and
- $R_3$ is a member of the group consisting of hydrogen and lower alkenoxy-carbonyl.

According to still another embodiment of the present invention, there is provided a method of manufacturing a medicament for substantially preventing a skin disorder characterized by substantially abnormal cell behavior, including the step of placing a pharmaceutically effective amount of a compound in a pharmaceutically acceptable carrier, the compound being a member of a group having a formula:

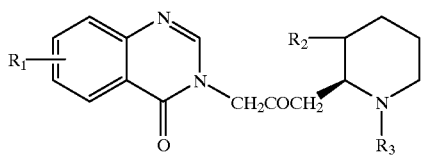

wherein:
- $R_1$ is a member of the group consisting of hydrogen, halogen, nitro, benzo, lower alkyl, phenyl, and lower alkoxy;
- $R_2$ is a member of the group consisting of hydroxy, acetoxy, and lower alkoxy, and
- $R_3$ is a member of the group consisting of hydrogen and lower alkenoxy-carbonyl.

According to another embodiment of the present invention, there is provided a method for the treatment of a skin disorder characterized by substantially abnormal cell behavior in a subject, including the step of administering to the subject a pharmaceutically effective amount of a compound having a formula:

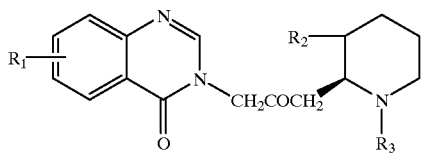

wherein:
- $R_1$ is a member of the group consisting of hydrogen, halogen, nitro, benzo, lower alkyl, phenyl and lower alkoxy;
- $R_2$ is a member of the group consisting of hydroxy, acetoxy and lower alkoxy, and
- $R_3$ is a member of the group consisting of hydrogen and lower alkenoxy-carbonyl.

In each of the embodiments above, preferably the compound is Halofuginone. Further preferably, the skin disorder is selected from the group consisting of psoriasis, keloid, hypertrophic scar, acne, seborrhea and alopecia. Most preferably, the skin disorder is selected from the group consisting of psoriasis, keloid and hypertrophic scar. Hereinafter, the term "keloid-like growth" includes keloid and hypertrophic scar.

BRIEF DESCRIPTION OF THE DRAWINGS

The invention is herein described, by way of example only, with reference to the accompanying drawings, wherein:

FIGS. 5A–5D show the inhibition of sulfate and glycine incorporation into rat mesengial cell ECM by Halofuginone.

DESCRIPTION OF THE PREFERRED EMBODIMENTS

Figure 1A:
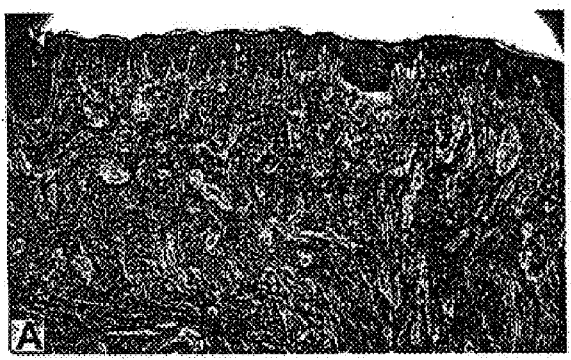
FIGS. 1A and 1B show collagen synthesis in keloid-derived tissue.

Unexpectedly, Halofuginone has been found to be an effective inhibitor of collagen synthesis by keloid-derived cells. Such an effect was not predicted by the prior art for the following reasons. First, the prior art did not teach the treatment of keloids or hypertrophic scars with Halofuginone. Second, keloids and hypertrophic scars arise from genetically abnormal skin cells. Thus, the behavior of these cells in response to Halofuginone cannot be predicted from the response of normal skin cells to Halofuginone. Third, keloids and hypertrophic scars are both characterized by the abnormal organization of collagen, as well as by over-synthesis of collagen. The prior art did not teach that Halofuginone would have any effect on pathological processes characterized by dysfunctional collagen fibril organization. Thus, the finding that Halofuginone is an effect inhibitor of keloid-related pathological processes is both novel and non-obvious.

Such a finding has implications for the treatment of other skin conditions as well, particularly psoriasis. As noted above, psoriasis is characterized by hyperplasia of the skin which is enabled by the deposition of excess extracellular matrix components (ECM), including collagen. Furthermore, psoriasis is also caused by genetically abnormal cells. Thus, the use of Halofuginone to treat psoriasis is novel and non-obvious for the following reasons. First, the prior art did not teach the treatment of psoriasis with Halofuginone. Second, the inhibitory effect of Halofuginone on ECM formation was also not suggested nor was it taught by the prior art, yet as detailed in the examples below, Halofuginone completely inhibits deposition of ECM components. Third, as noted above, Halofuginone can alter the behavior of genetically abnormal skin cells, an effect which was not taught by the prior art.

Other examples of skin disorders which could be amenable to treatment with Halofuginone include acne, seborrhea and alopecia. These conditions all reflect abnormal skin cell environments. For example, acne is a disorder characterized by excess oil production by the skin, leading to bacterial infection and scar formation if untreated. However, the excess oil production is promoted by the influence of hormones on skin cells, which is one reason adolescents tend to be most affected. Such hormones cause an abnormal environment for the skin cell, so that it in turn behaves abnormally. As noted above, Halofuginone has been shown to be effective in the control and inhibition of abnormal skin cell behaviors. Thus, Halofuginone is also a treatment for disorders, such as acne, characterized by such abnormal skin cell behavior.

Halofuginone can therefore be used to both prevent the clinical manifestations of skin disorders such as keloids, hypertrophic scars, psoriasis and acne, and to alleviate these disorders once they have arisen. For example, as detailed below, Halofuginone has been shown to be effective as a pretreatment, before surgery, for another surgically-induced pathological process, the formation of adhesions. Thus, Halofuginone is effective as a pretreatment before the appearance of clinical symptoms, as well as being able to alleviate or substantially eliminate such symptoms after they appear.

The present invention may be more readily understood with reference to the following illustrative examples and figures. It should be noted that although reference is made exclusively to Halofuginone, it is believed that the other quinazolinone derivatives described and claimed in U.S. Pat. No. 3,320,124, the teachings of which are incorporated herein by reference, have similar properties.

EXAMPLE 1

Collagen Synthesis in Keloid-Derived Tissue

Figure 1B:
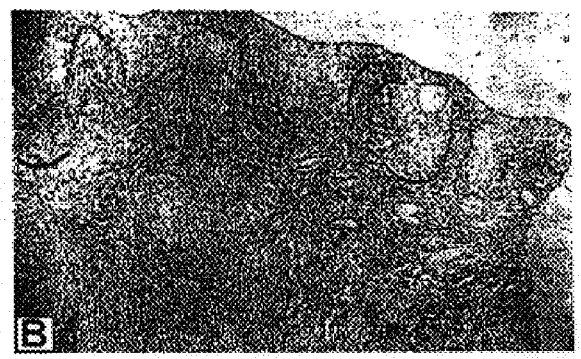

The presence of large amounts of collagen protein, as well as of the expression of the collagen α1(I) gene, were demonstrated in keloid-derived tissue. The results are shown in FIGS. 1A and 1B. The experiment was conducted as follows.

A keloid, which had arisen in response to the piercing of the ear for insertion of an earring, was removed from the ear lobe of a 21 year-old male. The keloid tissue was sectioned so that histological studies could be performed. Briefly, the tissue samples were collected into phosphate-buffered saline (PBS) and fixed overnight in 4% paraformaldehyde in PBS at 4° C. Serial 5 um sections were prepared after the samples had been dehydrated in graded ethanol solutions, cleared in chloroform and embedded in Paraplast. Differential staining of collagenous and non-collagenous proteins was performed with 0.1% Sirius red and 0.1% fast green as a counter-stain in picric acid. This procedure stains collagen red [Gascon-Barre, M., et al., J. Histochem. Cytochem., Vol 37, p. 377–381, 1989].

For hybridization with the genetic probe, the sections were deparafinized in xylene, rehydrated through a graded series of ethanol solutions, rinsed in distilled water for 5 minutes and then incubated in 2x SSC at 70° C. for 30 minutes. The sections were then rinsed in distilled water and treated with pronase, 0.125 mg/ml in 50 mM Tris-HCl, 5 mM EDTA, pH 7.5, for 10 minutes. After digestion, the slides were rinsed with distilled water, post-fixed in 10% formalin in PBS and blocked in 0.2% glycine. After blocking, the slides were rinsed in distilled water, rapidly dehydrated through graded ethanol solutions and air-dried for several hours. Before hybridization, the 1600 bp rat collagen α1(I) insert was cut out from the original plasmid, pUC18, and inserted into the pSafyre plasmid. The sections were then hybridized with this probe after digoxigenin-labelling. Alkaline phosphatase activity was detected in the sections as previously described [Knopov, V., et al., Bone, Vol 16, p. 329S–334S, 1995].

FIG. 1A shows a section of tissue taken from the keloid and stained with Sirius red. Most of the keloid tissue was stained with Sirius red except the epidermis, indicating the presence of high concentrations of collagen within the tissue. FIG. 1B shows the presence of cells, probably fibroblasts, which express high levels of the collagen α1(I) gene. Thus, clearly the keloid tissue was actively synthesizing collagen and expressing the type I collagen gene.

EXAMPLE 2

Figure 2:
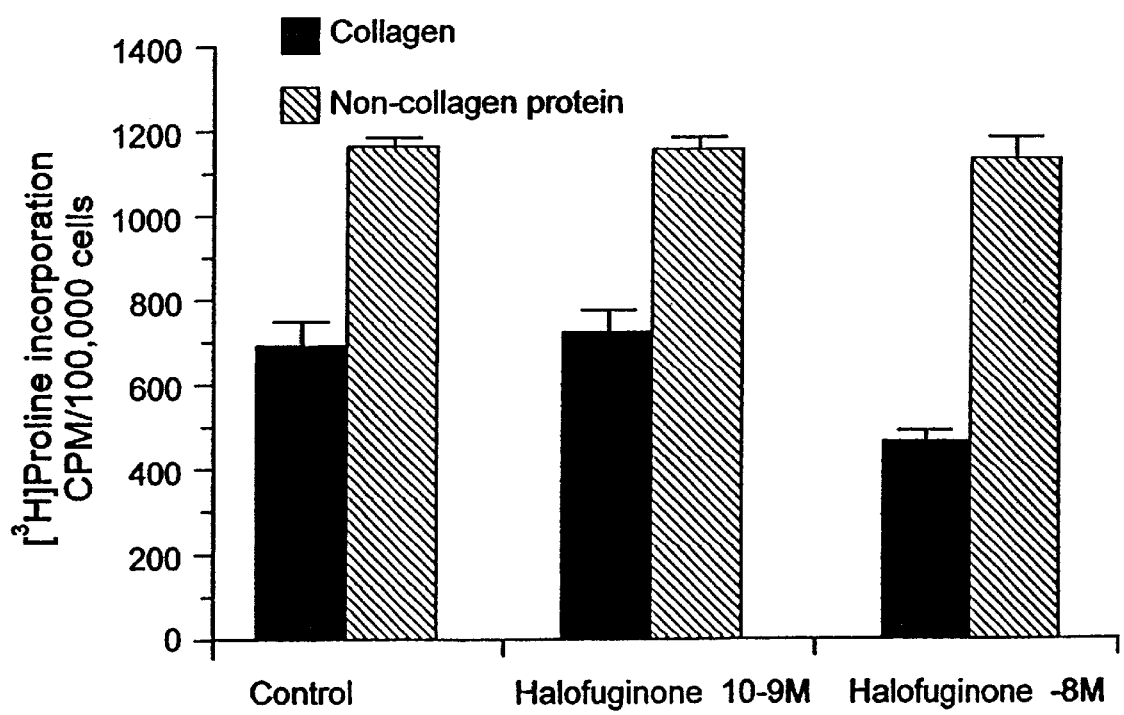
FIG. 2 illustrates the inhibitory effect of Halofuginone on collagen synthesis in keloid-derived tissue.

Inhibitory Effect of Halofuginone on Collagen Synthesis in Keloid-Derived Tissue Halofuginone was shown to specifically inhibit collagen synthesis in keloid-derived tissue. The results are shown in FIG. 2. The experiment was conducted as follows.

The keloid was removed as described in Example 1 above. The keloid-derived cells were incubated with and without Halofuginone for 24 hours in 0.5 ml glutamine-free DMEM containing 5% FCS (Fetal Calf Serum), ascorbic acid (50 $\mu$g/ml), B-aminopropionitrile (50 $\mu$g/ml) and 2 $\mu$Ci of [$^3$H]proline. At the end of incubation, the medium was decanted and the cells were incubated with or without collagenase for 18 hours, followed by precipitation of proteins by the addition of TCA (trichloroacetic acid). The amount of radiolabelled collagen was estimated as the difference between total labelled-proline containing proteins and those left after collagenase digestion [Granot, I. et al., Mol. Cell Endocrinol., Vol. 80, p. 1–9, 1991].

The ratio of collagenase digestible to non-collagenase digestible proteins was found to be higher in the keloid-derived cells than the usual values for normal skin cells. However, FIG. 2 shows that Halofuginone inhibited the production of collagen, but not of non-collagenase digestible proteins. Thus, Halofuginone specifically inhibited collagen synthesis in keloid-derived cells, and not total protein synthesis.

EXAMPLE 3

Halofuginone Inhibition of Sulfate Incorporation into ECM of Cultured Endothelial Cells As noted above, skin cell hyperproliferation is enabled by the deposition of ECM components. The following examples illustrate the ability of Halofuginone to inhibit such deposition of ECM components, further supporting the use of Halofuginone as a treatment for psoriasis. These examples illustrate the unexpected finding that Halofuginone completely abolishes deposition of all ECM components, and not just collagen, thereby preventing cell proliferation which is enabled by the formation of ECM.

Cultures of bovine corneal endothelial cells were established from steer eyes and maintained as previously described [D. Gospodarowicz, et al., Exp. Eye Res., No. 25, pp. 75–99 (1977)]. Cells were cultured at 37° C. in 10% $CO_2$ humidified incubators and the experiments were performed with early (3–8) cell passages.

For preparation of sulfate-labelled ECM (extra-cellular matrix), corneal endothelial cells were seeded into Swell plates at a confluent density forming, within 4–6 h, a contact inhibited cell monolayer composed of closely apposed, and growth arrested cells. Under these conditions, the cells remained viable and retained their normal monolayer configuration and morphological appearance up to a concentration of 2 μg/ml halofuginone. $Na_2[^{35}S]O_4$ (540–590 mCi/mmol) was added (40 μCi/ml) one and five days after seeding and the cultures were incubated without medium change. At various intervals after seeding, the subendothelial ECM was exposed by dissolving (5 min., room temperature) the cell layer with PBS containing 0.5% Triton X-100 and 20 mM NH4OH, followed by four washes in PBS [I Vlodavsky, et al., *Cancer Res.*, Vol. 43, pp 2704–2711 (1983); I. Vlodavsky, et al., *Proc. Natl. Acad. Sci. USA*, Vol. 84 pp. 2292–2296 (1987)). To determine the total amount of sulfate labeled material, the ECM was digested with trypsin (25 μg/ml 24 h, 37° C.) and the solubilized material counted in a β-counter.

Figure 3:
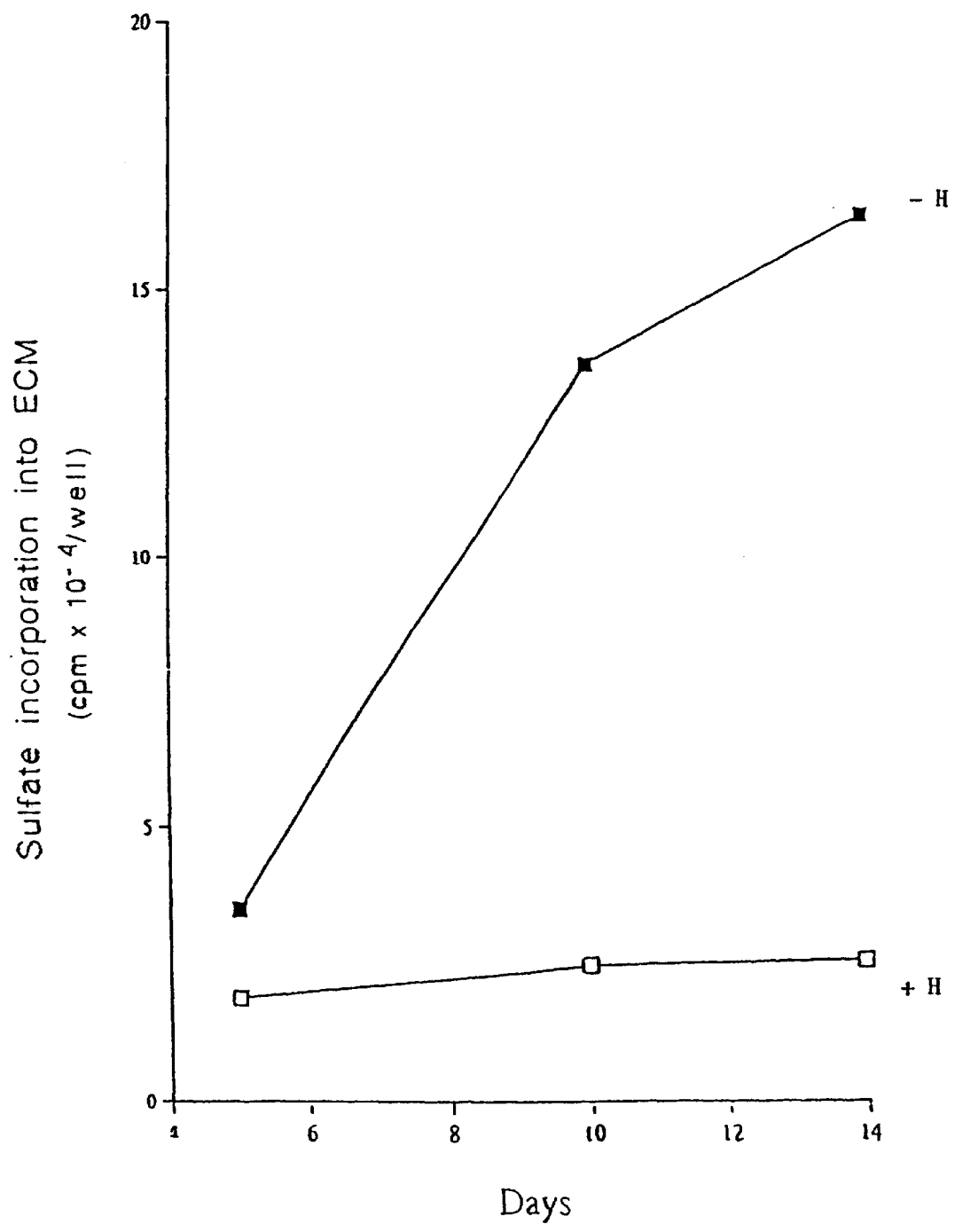
FIG. 3 shows Halofuginone inhibition of sulfate incorporation into ECM of cultured endothelial cells.

FIG. 3 shows the almost complete inhibition of sulfate incorporation by 1 μg/ml Halofuginone, while 50% inhibition was obtained in the presence of 0.2 μg/ml of the drug.

EXAMPLE 4

Figure 4:
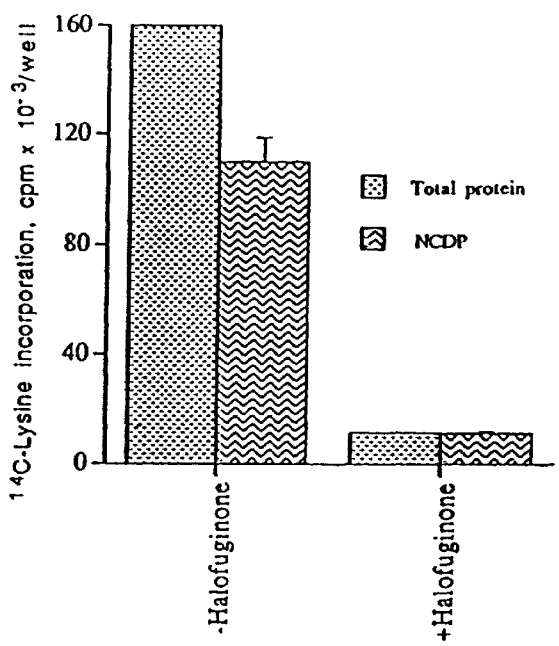
FIGS. 4A–4D show inhibition of incorporation of sulfate, proline, lysine and glycine into ECM of bovine corneal endothelial cells by Halofuginone.
Figure 4:
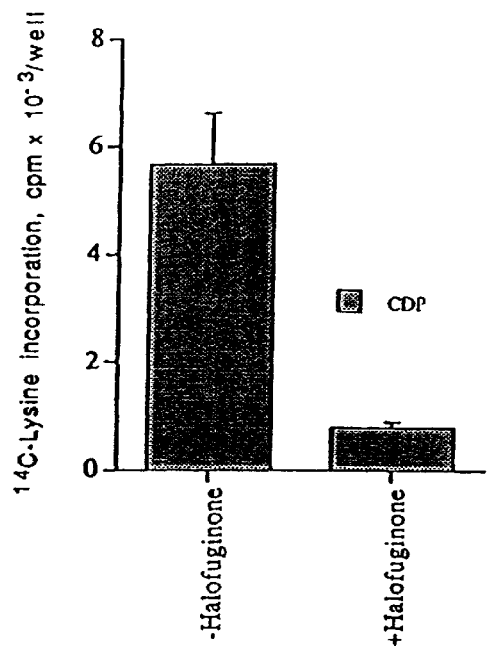
Figure 4:
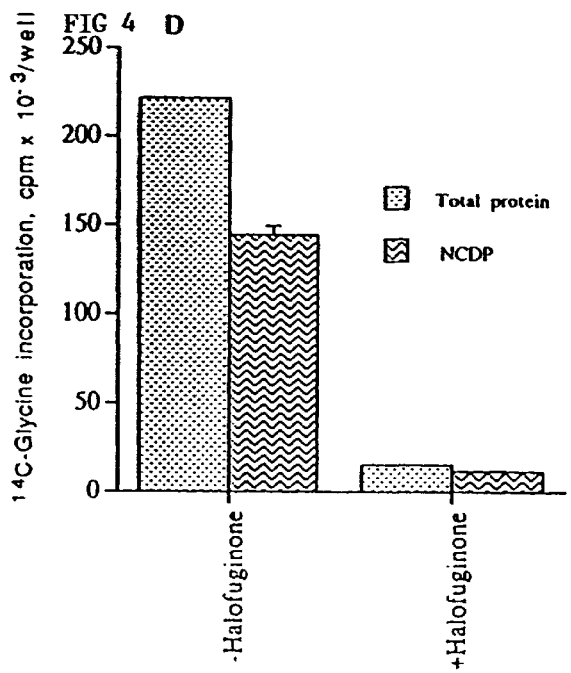
Figure 4:
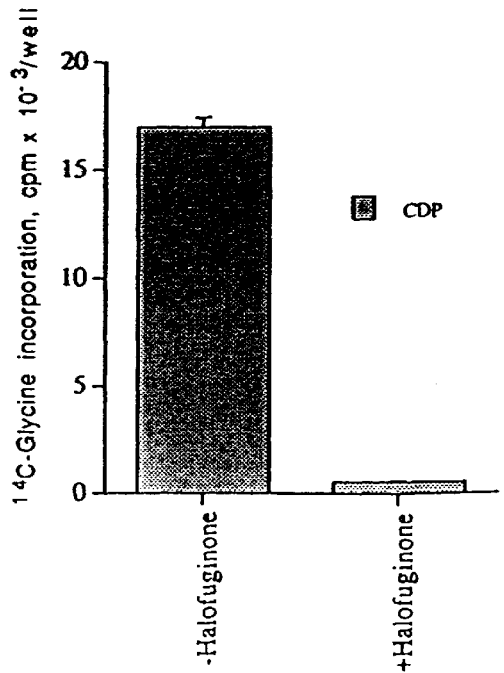

Inhibition of Incorporation of Sulfate, Proline, Lysine and Glycine into ECM of Bovine Corneal Endothelial Cells Corneal endothelial cells were seeded at a confluent density and grown as described in Example 3 above. The cells were cultured with or without Halofuginone in the presence of either $Na_2^{35}SO_4$ (FIG. 4A), $^3$H-proline (FIG. 4B), $^{14}$C-lysine (FIG. 4C) or $^{14}$C-glycine (FIG. 4D). Eight days after seeding, the cell layer was dissolved substantially as described in Example 3 above. The underlying ECM was then either trypsinized to determine the effect of Halofuginone on incorporation of labeled material into total protein, substantially as described in Example 3 above, or subjected to sequential digestions with collagenase and trypsin to evaluate the effect of Halofuginone on both collagenase-digestible proteins (CDP) and non-collagenase digestible proteins (NCDP).

As FIGS. 4A–4D show, Halofuginone inhibited the incorporation of sulfate, proline, lysine and glycine into both CDP and NCDP, reflecting a profound inhibition of matrix deposition. The inhibitory effect of Halofuginone on deposition of ECM components other than collagen is most likely due to the involvement of collagen in the assembly of other constituents into the supramolecular structure of the ECM. Alternatively, Halofuginone may affect the synthesis of ECM components other than collagen, possibly through a common transcription factor or cytokine such as TGFβ, which affects the synthesis and deposition of several ECM components.

EXAMPLE 5

Inhibition of Sulfate and Glycine Incorporation into Rat Mesengial Cell ECM

Rat mesengial cells were grown to confluency, 24 hours after seeding. The cells were then cultured with or without Halofuginone in the presence of either $Na_2^{35}SO_4$ (FIGS. 5A and 5B) or $^{14}$C-glycine (FIGS. 5C and 5D). Eight days after seeding, the cell layer was dissolved to expose the underlying ECM, washed and digested with collagenase to determine the effect of Halofuginone on CDP proteins, as shown in FIGS. 5A and 5C. The remaining material was digested with trypsin and subjected to β-scintillation counting to determine the effect of Halofuginone on NCDP proteins, as shown in FIGS 5B and 5D.

About 30% inhibition of sulfate incorporation was seen for CDP proteins, while about 70% inhibition was seen for NCDP proteins in the presence of 200 ng/ml Halofuginone. It should be noted that the inhibition of ECM deposition by Halofuginone was not due to its anti-proliferative activity since the drug was added to highly confluent, non-dividing cells. Since inorganic sulfate is incorporated primarily into sulfated glycosaminoglycans and not into collagen, it is conceivable that by inhibiting type I collagen synthesis, Halofuginone interferes with the assembly of other ECM macromolecules, such as heparin sulfate proteoglycans, which are known to specifically interact with collagen to form ECM.

About 80% inhibition of glycine incorporation was seen for both CDP and NCDP proteins in the presence of 50 ng/ml Halofuginone. The inhibitory effect of Halofuginone on deposition of collagenase-digestible ECM proteins was more pronounced with glycine than with sulfate labeled matrix since unlike glycine, sulfate is incorporated primarily into glucosaminoglycans which are not degraded by collagenase. A profound inhibition of ECM deposition was supported by a microscopic examination of the denuded culture dishes, revealing a thin or non-existant layer of ECM produced in the presence of Halofuginone.

EXAMPLE 6

Halofuginone as a Pretreatment

As noted above, Halofuginone has unexpectedly been shown to be effective as a pretreatment for the prevention of a surgically-induced pathological process, the formation of adhesions. Such an effect also has implications for the prevention of surgically-induced keloids and hypertrophic scars. The results of pretreatment with Halofuginone are given in Table 1 below.

The experimental method was as follows. Halofuginone was administered in the diet of two groups of rats at a concentration of 5 mg/kg dry feed for 4 days before surgery, as a pretreatment. Two other groups of rats were fed a normal diet and served as control groups. One of the groups of rats fed Halofuginone and one control group then underwent surgery, which was performed as follows. First, the abdomen of the rats was shaved and prepared with iodine and alcohol. The abdominal cavity was entered through a mid-line incision. The small intestine was scraped from the duodenum down to from about 9 to about 10 cm from the cecum, until capillary bleeding occurred. To avoid drying, Hartman's solution at about 37 C. was occasionally dripped on the intestine. After replacement of the intestine into the abdominal cavity, the abdomen was closed in two layers with continuous 00 chromic catgut suture. This method has been previously demonstrated to cause abdominal adhesions (Rivkind, A. I. et al., Eur. Surg. Res., Vol 17, p. 254–258, 1985].

In those rats receiving the drug, Halofuginone treatment was continued for 21 days following surgery. At the end of 21 days, the rats were weighed and the number and severity of adhesions were determined according to a double-blind procedure, in which adhesions were classified according to the following grading: 0=no adhesions; I=a thin, filmy, easily separated adhesion; II=several thin adhesions; III=a thick, broad adhesion and IV=several thick adhesions. Clearly, 0 is the least severe and IV is the most severe grade.

Table 1 shows the effect of Halofuginone on adhesion formation. None of the rats without surgical intervention, either with or without Halofuginone treatment, had any adhesions. However, with one exception, all of the rats which underwent surgical intervention, but which were not treated with Halofuginone, had at least one adhesion. Most of the adhesions were between loops of the small bowels and at least one was between the small bowel and the omentum. By contrast, a smaller number Halofuginone-treated rats which underwent surgery had an adhesion, and the adhesions were more mild. Thus, clearly Halofuginone administered in the diet, similar to the administration to chickens as a coccidostat, was able to inhibit post-surgical adhesion formation in rats. Furthermore, weight gain by all of the different groups of rats was substantially similar, showing that the effect of Halofuginone was specific and did not result in any general reduction in overall well-being of the rats.

TABLE 1

Effect of Halofuginone in Diet on Adhesion Number and Severity

| Group Number | Weight Gain (g/21 days) | Adhesion Score |
|---|---|---|
| 1 | 70 | 1–2 |
| 1 | 73 | 1 |
| 1 | 80 | 0 |
| 1 | 87 | 1–2 |
| 1 | 93 | 3–4 |
| 1 | 83 | 3 |
| 1 | 92 | 1–2 |
| 1 | 109 | 1–2 |
| 1 | 113 | 3 |
| 1 | 77 | 1–2 |
| 2 | 86 | 0–1 |
| 2 | 76 | 0 |
| 2 | 61 | 1 |
| 2 | 80 | 1–2 |
| 2 | 80 | 0 |
| 2 | 65 | 0 |
| 2 | 90 | 1 |
| 2 | 80 | 0–1 |
| 2 | 79 | 0–1 |
| 2 | 63 | 1–2 |
| 3 | 102 | 0 |
| 3 | 70 | 0 |
| 3 | 73 | 0 |
| 3 | 98 | 0 |
| 3 | 72 | 0 |
| 3 | 90 | 0 |
| 3 | 80 | 0 |
| 3 | 76 | 0 |
| 3 | 85 | 0 |
| 3 | 83 | 0 |
| 4 | 93 | 0 |
| 4 | 80 | 0 |
| 4 | 85 | 0 |
| 4 | 115 | 0 |
| 4 | 100 | 0 |
| 4 | 60 | 0 |
| 4 | 100 | 0 |
| 4 | 102 | 0 |
| 4 | 105 | 0 |
| 4 | 68 | 0 |

EXAMPLE 7

Suitable Formulations for Administration of Halofuginone

Halofuginone can be administered to a subject in a number of ways, which are well known in the art. Hereinafter, the term "subject" refers to the human or lower animal to whom Halofuginone was administered. For example, administration may be done topically (including ophtalmically, vaginally, rectally, intranasally), orally, or parenterally, for example by intravenous drip or intraperitoneal, subcutaneous, or intramuscular injection.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

Dosing is dependent on the severity of the symptoms and on the responsiveness of the subject to Halofuginone. Persons of ordinary skill in the art can easily determine optimum dosages, dosing methodologies and repetition rates.

EXAMPLE 8

Methods of Treatment of Skin Disorders

As noted above, Halofuginone has been shown to be an effective inhibitor of the clinical etiology of skin disorders, such as keloid and hypertrophic scar formation. The following examples are illustrations only of methods of treating skin disorders characterized by abnormal skin cell behavior with Halofuginone, and are not intended to be limiting.

The method includes the step of administering Halofuginone, in a pharmaceutically acceptable carrier as described in Example 7 above, to a subject to be treated. Halofuginone is administered according to an effective dosing methodology, preferably until a predefined endpoint is reached, such as the absence of symptoms of a skin disorder in the subject. For example, if a subject already had a keloid, the endpoint could be the reduction in size of the keloid or its elimination.

Halofuginone can also be used as a pretreatment, administered to a subject before surgery to substantially prevent the formation of keloids or hypertrophic scars. Of course, such a pretreatment would be most effective for scheduled surgery, as that would allow Halofuginone to be administered for a sufficient period of time before surgery to be most effective.

EXAMPLE 9

Method of Manufacture of a Medicament Containing Halofuginone

The following is an example of a method of manufacturing Halofuginone. First, Halofuginone is synthesized in accordance with good pharmaceutical manufacturing practice. Examples of methods of synthesizing Halofuginone, and related quinazolinone derivatives, are given in U.S. Pat. No. 3,338,909. Next Halofuginone is placed in a suitable pharmaceutical carrier, as described in Example 7 above, again in accordance with good pharmaceutical manufacturing practice.

While the invention has been described with respect to a limited number of embodiments, it will be appreciated that many variations, modifications and other applications of the invention may be made.

What is claimed is:

1. A method for the treatment of psoriasis in a subject, the method comprising the step of administering to the subject a pharmaceutically effective amount of a compound having a formula:

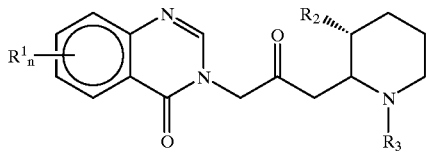

wherein:

R₁ is a member of the group consisting of hydrogen, halogen, nitro, benzo, lower alkyl, phenyl and lower alkoxy;

R₂ is a member of the group consisting of hydroxy, acetoxy and lower alkoxy, and R₃ is a member of the group consisting of hydrogen and lower alkenoxy-carbonyl.

2. The method of claim 1, wherein said compound is Halofuginone.

3. The method of claim 1, wherein said compound is administered to the subject by a route selected from the group consisting of oral, parenteral and topical.

4. The method of claim 3, wherein said compound is administered to the subject by topical application.

5. The method of claim 4, wherein said compound is contained in a pharmaceutical carrier selected from the group consisting of a lotion, an ointment, a gel, a cream, a liquid and a spray.

6. The method of claim 5, wherein the step of administering said compound to the subject is performed until symptoms of psoriasis are absent in the subject.

* * * * *